US008137660B1

(12) United States Patent
Whitehead et al.

(10) Patent No.: US 8,137,660 B1
(45) Date of Patent: Mar. 20, 2012

(54) APPLICATION OF TANNINS TO REDUCE ODOR EMISSIONS FROM ANIMAL WASTE

(75) Inventors: Terence R. Whitehead, Peoria, IL (US); Michael A. Cotta, Edelstein, IL (US); Cheryl Spence, Hanna City, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 293 days.

(21) Appl. No.: 12/487,153

(22) Filed: Jun. 18, 2009

Related U.S. Application Data

(60) Provisional application No. 61/159,199, filed on Mar. 11, 2009.

(51) Int. Cl.
*A61L 11/00* (2006.01)
*A61K 9/00* (2006.01)
(52) U.S. Cl. ...................... 424/76.6; 424/400
(58) Field of Classification Search .................. 424/400, 424/76.6
See application file for complete search history.

(56) References Cited

U.S. PATENT DOCUMENTS

| | | | | |
|---|---|---|---|---|
| 6,902,726 | B1 * | 6/2005 | Varel ............................. | 424/76.6 |
| 2001/0011646 | A1 * | 8/2001 | Moore, Jr. ...................... | 210/724 |
| 2007/0136835 | A1 * | 6/2007 | Dandekar et al. ............. | 800/278 |
| 2009/0285931 | A1 * | 11/2009 | Shelby et al. ...................... | 426/2 |

OTHER PUBLICATIONS

Hess et al. ("Strategic use of tannins as a means to limit methane emission from ruminant livestock" in International Congress Series (2006), 164-167).*

Animut et al. ("Methane emission by goats consuming different sources of condensed tannins," in Animal Feed Science and Technology, 144 (2008) 228-241.*

Coulis et al. ('Fate of condensed tannins during litter consumption by soil animals, in Soil Biology and Biochemistry, 41,( 2009), 2573-2578.*

Hawley's Condensed Chemical Dicitonary, Fourteenth Edition, John Wiley & Sons, New York 2001, p. 1068.

Beauchemin, K. A., et al, "Use of condensed tannin extract from quebracho trees to reduce methane emissions from cattle", Journal of Animal Science, 85, pp. 1990-1996.

Hall-Larsson, Katarina, "Effects of different forages on production of hydrogen sulphide in a rumen in vitro system", Sweedish University of Agricultural Sciences, Dpt. of Animal Nutrition & Management, Examensarbete 196, Uppsala 2004, pp. 1-34.

Field, J. et al, "Continuous Anaerobic Treatment of Autoxidized Bark Extracts in Laboratory-Scale Columns", Biotechnology & Bioengineering, vol. 32, pp. 247-155, 1991.

Carulla, J. E., et al., "Supplementation of Acadia mearnsii tannins decreases methanogenesis and urinary nitrogen in forage-fed sheep", Australian Journal of Agricultural Research, 2005, 56, pp. 961-970.

(Continued)

*Primary Examiner* — Blessing Fubara
(74) *Attorney, Agent, or Firm* — John Fedo; Randall E. Deck; Lesley Shaw

(57) ABSTRACT

Quebracho tannins are effective for the treatment of animal wastes which contain feces or fecal waste-containing material to inhibit odor emissions therefrom. Application of an effective amount of Quebracho tannins to the animal wastes elicits one or both of reducing gas emissions (such as total gas, hydrogen sulfide, and/or methane) therefrom, and reducing the populations or metabolic activity of anaerobic sulfate reducing bacteria therein. Reduction of odor emissions from the animal waste may also be effected by combining the Quebracho tannins with animal litter which is applied in the locus or vicinity of the animal.

19 Claims, 4 Drawing Sheets

OTHER PUBLICATIONS

Vijayaraghavan, K., et al., "Effect of toxic substances in anaerobic treatment o ftannery wastewaters", Bioprocess Engineering 16, 1997, pp. 151-155.

Bae, Hee Dong, et al, "Effects of Condensed Tannins on Endoglucanase Activity and Filter Paper Digestioin by *Fibrobacter succinogenese* S85", Applied and Environmental Microbiology, Jul. 1993, vol. 59, No. 7, pp. 2132-2138.

Cook, Kimberly, et al., "Development of a Real-Time Pcr Assay for Detection of Sulfate-Reducing Bacteria in Stored Swine Manure and Swine Feces", abstract, American Society for Microbiology, May 27, 2004, Paper No. Q-093.

Cook, Kimberly et al, "Detection of Sulfate Reducing Bacteria in Stored Swine Manure Using Quantititve, Real-Time Pcr Analysis", abstract, Microbial Ecology International Symposium, Paper No. 226, Aug. 27, 2004.

Whitehead, Terence, et al., "Identification of Sulfate-Reducing Bacteria from Stored Swine Manure by Pure Culture Isolation and Direct Dsra Pcr", abstract, Microbial Ecology International Symposium, Aug. 27, 2004, Paper No. 228.

Whitehead, Terence R., et al, "Pure culture and pcr analyses of sulfate-reducing bacteria from swine feces and stored swine manure", abstract, Reproduction Nutrition Development, Jun. 9, 2004, 44(1), p. S32.

Cook, Kimberly, et al., "Variability in the Concentration of Sulfate-Reducing Bacteria in Swine Manure and Feces as Determined Using a Real-Time Pcr Assay", abstract, Reproduction Nutrition Development, Jun. 7, 2004, 44(1), 56.

* cited by examiner

A.

B.

C.

SEQUENCE LISTING

```
<160> NUMBER OF SEQ ID NOS: 9

<210> SEQ ID NO 1
<211> LENGTH: 19
<212> TYPE: DNA
<213> ORGANISM: Desulfobulbus sp.

<400> SEQUENCE: 1
gygagtggkc ctgctayga                                              19

<210> SEQ ID NO 2
<211> LENGTH: 18
<212> TYPE: DNA
<213> ORGANISM: Desulfobulbus sp.

<400> SEQUENCE: 2
ccaggtgccg ataacrgc                                               18

<210> SEQ ID NO 3
<211> LENGTH: 19
<212> TYPE: DNA
<213> ORGANISM: Desulfovibrio sp.

<400> SEQUENCE: 3
cgacacccar gacatgtgc                                              19

<210> SEQ ID NO 4
<211> LENGTH: 20
<212> TYPE: DNA
<213> ORGANISM: Desulfovibrio sp.

<400> SEQUENCE: 4
gcwgctacgc aaccgttggg                                             20

<210> SEQ ID NO 5
<211> LENGTH: 20
<212> TYPE: DNA
```

-continued

```
<213> ORGANISM: Desulfovibrio sp.

<400> SEQUENCE: 5
ctgcgaatat gcctgctaca                                            20

<210> SEQ ID NO 6
<211> LENGTH: 19
<212> TYPE: DNA
<213> ORGANISM: Desulfovibrio sp.

<400> SEQUENCE: 6
ggggcarccg tcgaacttg                                             19

<210> SEQ ID NO 7
<211> LENGTH: 16
<212> TYPE: DNA
<213> ORGANISM: Artificial
<220> FEATURE:
<223> OTHER INFORMATION: Specific primers for amplifying all bacterial
      16S rRNA genes by PCR-based methods

<400> SEQUENCE: 7
atggctgtcg tcagct                                                16

<210> SEQ ID NO 8
<211> LENGTH: 15
<212> TYPE: DNA
<213> ORGANISM: Artificial
<220> FEATURE:
<223> OTHER INFORMATION: Specific primers for amplifying all bacterial
      16S rRNA genes by PCR-based methods

<400> SEQUENCE: 8
acgggcggtg tgtac                                                 15

<210> SEQ ID NO 9
<211> LENGTH: 15
<212> TYPE: DNA
<213> ORGANISM: Artificial
<220> FEATURE:
<223> OTHER INFORMATION: Specific primers for amplifying all bacterial
      16S rRNA genes by PCR-based methods

<400> SEQUENCE: 9
caacgagcgc aaccc                                                 15
```

APPLICATION OF TANNINS TO REDUCE ODOR EMISSIONS FROM ANIMAL WASTE

CROSS REFERENCE TO RELATED APPLICATION

This application claims the benefit under 35 U.S.C. 1.19(e) of U.S. provisional No. 61/159,199, filed Mar. 11, 2009, the contents of which are incorporated by reference herein.

BACKGROUND OF THE INVENTION

1. Field of the Invention

The invention is drawn to a method for controlling the odor emissions from animal waste.

2. Description of the Prior Art

Swine and other livestock are commonly reared in facilities that are specially designed to manage manure and liquid waste generated by such livestock. For example, in some swine rearing facilities, swine are raised in enclosed facilities that have slatted floors. Beneath the floors are pits for receiving swine manure and urine that pass through the slatted floor. These pits contain water that is occasionally drained to remove the livestock waste. Other facilities raise swine on a hard slanted floor, and periodically wash accumulated manure and urine from the slanted floor. Still other facilities use a combined approach, and have slatted floors on which the swine are raised, and a slanted floor underneath that is periodically washed to remove accumulated manure and urine. Water that is used to flush manure in these facilities is often pumped into large tanks that can be quickly discharged to rapidly flush manure from the facility.

Dairy cows are also often raised in facilities that must periodically be washed of animal manure and urine. The dairy cows are often fed in a sheltered pen that has a hard concrete floor that is periodically washed.

Manure excreted by the livestock generate hydrogen sulfide, methane, ammonia, volatile fatty acids, phenols, and other gases that contribute to the offensive odor in many livestock rearing facilities. The emitted hydrogen sulfide can also pose a health risk to workers as well as the animals. Hydrogen sulfide is being considered as a regulatory standard to monitor emissions from swine facilities. Production of $H_2S$ involves sulfate reduction largely by anaerobic sulfate-reducing bacteria (SRB). Previous studies by Cook et al. (for example, 2004, Detection of Sulfate-Reducing Bacteria in Stored Swine Manure Using Quantitative Real-Time PCR Analysis, Microbial Ecology International Symposium paper no. 2260) and Whitehead et al. (for example, 2004, Pure Culture and PCR Analyses of Sulfate-Reducing Bacteria from Swine Feces and Stored Swine Manure, Reproduction Nutrition Development 44:S32) began to uncover the diversity of SRB in stored swine manure using a phylogenetic and molecular based approach. Phylogenetic analysis of cloned dissimilitory sulfite reductase A (dsrA) genes identified 3 major groups of SRB in swine manure with high similarity to *Desulfobulbus* and *Desulfovibrio*-like species.

Numerous management strategies, technologies, and chemicals have been used to try to reduce these gases. However, many of these are usually either too toxic to the animals, not cost effective or not environmentally sustainable. Thus, the need remains for improved techniques for reducing offensive odors generated from animal wastes.

SUMMARY OF THE INVENTION

We have now discovered that Quebracho tannins are effective for the treatment of animal wastes which comprise feces or fecal waste-containing material to inhibit odor emissions therefrom. In the process of the invention, application of an effective amount of Quebracho tannins to the animal wastes elicits one or both of reducing gas emissions (such as total gas, hydrogen sulfide, and/or methane) therefrom, or reducing the populations or metabolic activity of anaerobic sulfate reducing bacteria therein. Reduction of odor emissions from the animal waste may also be effected by combining the Quebracho tannins with animal litter which is applied in the locus or vicinity of the animal.

In accordance with this, it is an object of this invention to provide an improved method for inhibiting the emission of hydrogen sulfide, methane, and other odorous and non-odorous gases from animal wastes using Quebracho tannins.

A further object of this invention is to provide an improved method for reducing the populations and/or metabolic activity of sulfate reducing bacteria in animal wastes.

It is another object of this invention to provide an improved method for inhibiting the emission of hydrogen sulfide, methane, and other odors from animal wastes using natural plant tannins which have a low impact on the environment.

Other objects and advantages of the invention will become apparent from the ensuing description.

DETAILED DESCRIPTION OF THE INVENTION

Figure 1:
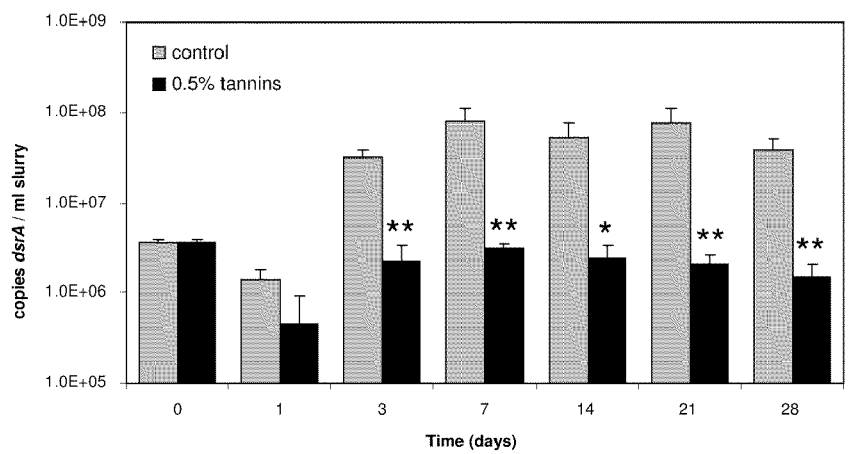
FIG. 1 shows the quantification of SRB in stored swine manure treated in vitro with 0.5% w/v condensed tannins in Example 1. Each treatment was performed in triplicate and data are presented as the mean of triplicate qRT-PCR assays. Significance values for comparisons of control versus tannin treatment: *, $P<0.05$; **, $P<0.01$.
Figure 1:
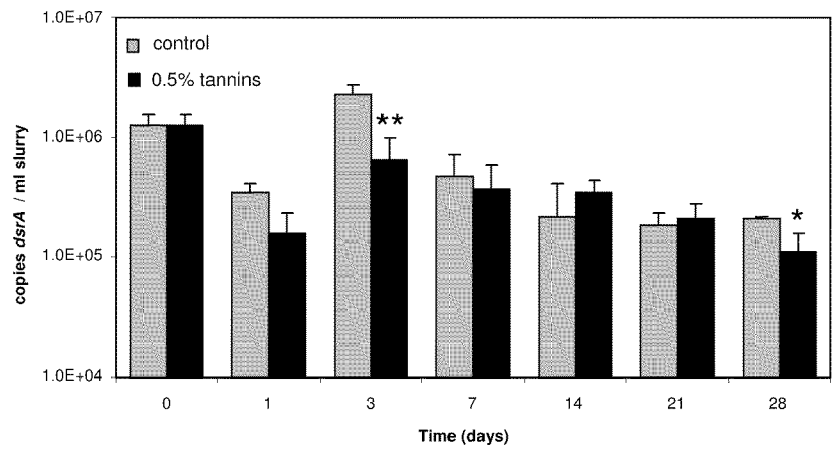
Figure 1:
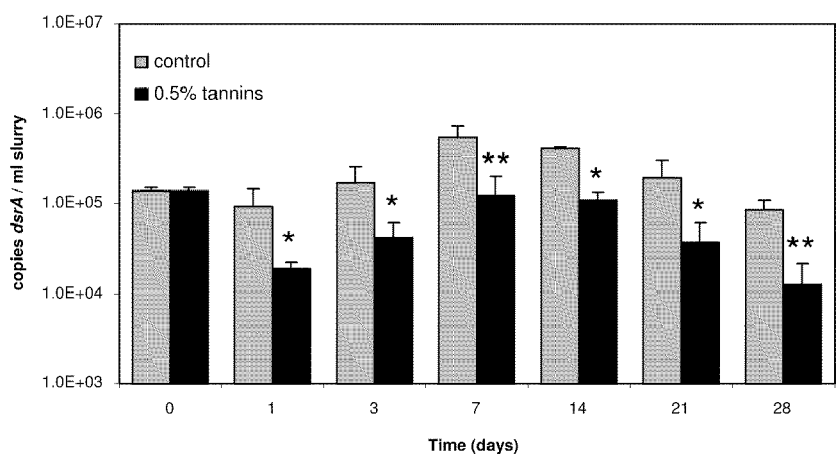

Tannins are astringent, bitter plant polyphenols that either bind and precipitate or shrink proteins. The astringency from the tannins is what causes the dry and puckery feeling in the mouth following the consumption of red wine or an unripened fruit. The term tannin refers to the use of tannins in tanning animal hides into leather; however, the term is widely applied to any large polyphenolic compound containing sufficient hydroxyls and other suitable groups (such as carboxyls) to form strong complexes with proteins and other macromolecules. Tannins have molecular weights ranging from 500 to over 9,000. Tannins are incompatible with alkalis, gelatin, heavy metals, iron, lime water, metallic salts, strong oxidizing agents and zinc sulfate. Tannins are usually divided into hydrolyzable tannins and condensed tannins (proanthocyanidins). Condensed tannins have been shown to have antibacterial properties and have been used in vitro in studies to reduce methane emissions and frothy bloat in cattle (Beauchemin et al. 2007. Use of condensed tannin extract from Quebracho trees to reduce methane emissions from cattle. J. Anim. Sci. 85:1900-1996; and Min et al. 2006. Effects of condensed tannins supplementation level on weight gain and in vitro and in vivo bloat precursors in steers grazing winter wheat. J. Anim. Sci. 84:2546-2554).

The tannins which are suitable for use herein are tannins derived from the Quebracho tree, including *Schinopsis* species, particularly *S. lorentzii* and *S. balansae*, as well as *Aspidosperma Quebracho-blanco*, which primarily grow in South America. Condensed Quebracho tannins are particularly preferred. Quebracho tannins have been widely used in the tanning of animal hides. We have surprisingly discovered that Quebracho tannins are significantly more effective than other tannins for reducing odor emissions from animal waste containing feces and fecal waste-containing materials. In accordance with this discovery, the application of an effective amount of Quebracho tannins onto the animal waste elicits one or more of the following effects in the treated waste: a) reducing total gas emissions therefrom, b) reducing hydrogen sulfide emissions therefrom, c) reducing methane emissions therefrom, d) reducing populations of anaerobic sulfate reducing bacteria therein, and e) reducing the metabolic activity of anaerobic sulfate reducing bacteria therein, all in comparison to an untreated control.

In a first preferred embodiment, the process of the invention is used for the treatment of feces or fecal waste-containing materials collected in a receptacle such as a cistern or tank (open or closed), pit, lagoon, holding pond or settling pond, such as from controlled animal rearing facilities or other facilities for permanently or temporarily holding animals, or from municipal waste treatment facilities. However, the process is particularly suited to the treatment of animal wastes from animal containment facilities used for the large-scale production of swine and cattle and the rearing of dairy cattle. While the treated animal waste may be solid feces (i.e., manure), the process is particularly suited to the treatment of waste materials present as liquid slurries of feces in urine, or feces and/or urine mixed with water or aqueous treatment solutions, such as that used for flushing feces and urine from controlled animal rearing or other facilities. The process may be used for the treatment of animal wastes generated by a variety of livestock, and domestic or wild animals, including but not limited to swine (e.g., pigs and hogs), bovine (e.g., cattle and dairy cows), fowl (e.g., poultry including chickens and turkeys), equine (e.g., horses), caprine (e.g., goats), ovine (e.g., sheep), feline (e.g., domestic cats), canine (e.g., domestic dogs), rodentia, leporids, mustelids or zoo animals.

In accordance with this first embodiment, the tannins may be applied directly on or into the animal waste to be treated. The tannins may be applied in substantially pure or crude form, or they may be formulated with an optional solid or liquid carrier for ease of application. As it is common practice in the art to collect, flush, or otherwise store animal wastes within the above-mentioned receptacles, it is understood that the tannins may be applied onto the surface of the waste contained in any of these sites. Furthermore, the tannins may be applied onto animal waste deposited upon litter, such as that used in poultry rearing facilities or commercial pet litter which is commonly used for collection of waste material from domestic pets such as cats, rodentia (e.g., guinea pigs, mice, hamsters, and gerbils), leporids (e.g., rabbits), and mustelids (e.g., ferrets). Alternatively, the tannins may be formulated in combination with liquid or aqueous compositions used to rinse or wash manure and/or urine from the floors, walls or other surfaces of the animal rearing facilities. To improve contact of the tannins with the waste material, and particularly the anaerobic sulfate reducing bacteria therein, the tannins may be mixed with the waste. Contact may be further improved by applying the tannins within the receptacle prior to the collection of the animal waste therein.

In an alternative preferred embodiment, the Quebracho tannins may be used in combination with the above-mentioned animal litter. In this embodiment, the litter is provided in the locus of an animal to receive the feces and/or urine discharged therefrom, typically on the floor of the animal rearing facility or within a dedicated waste receptacle such as a "litter box". The particular litter used is not critical, and a variety of conventional animal litters are suitable for use herein. By way of example and without being limited thereto, litter used in poultry rearing operations may include one or more of recycled paper, straw, wood shavings, saw dust, rice hulls or peanut hulls, while commercial pet litter may include granular or particulate clays, calcium bentonite, bentonite clay, diatomaceous earth, quartz, silicates, and mixtures thereof. While the tannins and litter may be formulated together for convenience, it is understood that they also may be applied separately.

The Quebracho tannins are applied in an amount effective to control odor emissions from animal waste. An effective amount is defined herein as that amount which will significantly reduce odor emission (i.e., production) from treated animal waste comprising feces or fecal waste-containing material, in comparison to untreated control animal waste. Without being limited thereto, this reduction of odor emissions may be demonstrated by one or more of the following: a) a significant reduction in total gas emissions therefrom, b) a significant reduction in hydrogen sulfide emissions therefrom, c) a significant reduction in methane emissions therefrom, d) a significant reduction in the populations of anaerobic sulfate reducing bacteria therein, and e) a significant reduction in the metabolic activity of anaerobic sulfate reducing bacteria therein, each in comparison with untreated controls. Suitable amounts may be readily determined by the practitioner skilled in the art, and will vary with the specific waste material, environmental conditions, and the duration of treatment. Measurements may be conducted using routine gas analysis and microbial analysis techniques known in the art or as described in the Examples. By way of example, and without being limited thereto, suitable amounts will typically be greater than or equal to about 0.1% (measured by weight of the Quebracho tannins per volume of animal waste, wherein 1%=1 g/100 ml). The upper limit of the amount of tannins is not critical, although the amount of tannins will typically be less than or equal to about 10% (measured by weight of the tannins per volume of animal waste). While greater amounts may be used, they may not be cost effective and are therefor not preferred. Preferred amounts for administration of the tannins are be greater than or equal to about 0.1% and less than or equal to about 1.0% (measured by weight of the Quebracho tannins per volume of animal waste). Application of the tannins may be repeated as necessary, particularly when storing animal waste for extended periods of time.

In addition to the Quebracho tannins, other additives and adjuncts may be formulated into the composition. Suitable additives may include, but are not limited to, oxidizing agents such as hydrogen peroxide or potassium permanganate, fungicides, fungistats, bactericides, bacteriostats, or combinations thereof.

It is understood that the foregoing detailed description is given merely by way of illustration and that modifications and deviations may be made therein without departing from the spirit and scope of the invention.

EXAMPLE 1

Swine Manure Samples and In Vitro Incubations

Swine manure slurry was collected from underground storage pits at a local swine facility in Eureka Ill. Slurry was diluted in anaerobic buffer to a 10% final solution and 100 ml aliquots were added to six 150 ml serum bottles under a stream of nitrogen. Three bottles were left untreated (control) and immediately sealed. To the remaining samples, 0.5% w/v Quebracho condensed tannins (Chemtan Company Inc, Exeter, N.H.) was added, mixed well to dissolve the tannins and then capped and sealed. All bottles were incubated anaerobically at room temperature for 28 days.

Detection of Hydrogen Sulfide:

$H_2S$ production was measured with a portable Jerome 631-X Hydrogen Sulfide analyzer (Arizona Instruments, Tempe, Ariz.). A gas tight syringe was used to remove a 1 ml volume of headspace gas at each time point. This was diluted into a known volume of air, mixed and analyzed for $H_2S$ concentration. Each analysis was performed in duplicate.

DNA Extraction from Swine Manure Slurry:

One ml aliquots of slurry were removed from samples at each time point and mixed with an equal volume of Tris-saturated phenol and 10% v/v zirconium beads (0.1 mm). Samples were homogenized for 30 s at a speed of 4 m/s in a FASTPREP Instrument (Q-BIOgene, Irvine, Calif.), followed by centrifugation for 10 min at 14,000×g. A 600 ul aliquot of the supernatant was then added to 500 ul FASTPREP Binding Matrix and extracted using the FASTDNA Spin kit (Q-BIOgene, Irvine, Calif.) according to the manufacturer's instructions.

Quantitative Real-Time PCR Analysis:

Real-time PCR assays were performed on a Rotorgene 6000 (Corbett Robotics Inc., San Francisco, Calif.), using the QuantiTect SYBR Green PCR kit (Qiagen, Valencia, Calif.), gene specific primers and 5:1 template DNA. Reaction conditions were 95° C. for 15 minutes (1×), then 95° C., 15 seconds, 59° C., 30 seconds, 72° C., 30 seconds (40×). For quantification of 16S rDNA, 5:1 template DNA was used in a reaction mixture containing 2× Quantitect Probe PCR Mastermix (Qiagen, Valencia, Calif.), gene specific primers and the 16STaq1115-BHQ probe. Reaction conditions for quantification of 16S rDNA were 95° C. for 15 minutes (1×), then 95° C., 15 seconds, 55° C., 60 seconds (40×). All samples were run in triplicate. For each of the three group dsrA assays, standard DNA consisted of plasmid carrying a dsrAB insert from previously sequenced cloned slurry samples. Bacterial 16S rRNA gene copy numbers were determined as previously described (Harms et al. 2003. Real-time PCR quantification of nitrifying bacteria in a municipal wastewater treatment plant. *Environ. Sci. Technol.* 37:343-351). Standard curves were generated from different concentrations of template DNA using the respective real-time PCR program for each primer set

TABLE 1

Oligonucleotide primers and probes used in this study for qRT-PCR.

| Primer | Assay | Target | Sequence (5'-3') | Amplicon length (bp) |
|---|---|---|---|---|
| Grp1fd | Group 1 | *Desulfobulbus*-like SRB | GYGAGTGGKCCTGCTAYGA | 172 |
| Grp1rd | | | CCAGGTGCCGATAACRGC | |
| Grp2fd | Group 2 | *Desulfovibrio*-like SRB | CGACACCCARGACATGTGC | 121 |
| Grp2rd | | | GCWGCTACGCAACCGTTGGG | |
| Grp3fw | Group 3 | *Desulfovibrio* Enrichment - | CTGCGAATATGCCTGCTACA | 119 |
| Grp3rd | | Culture SRB | GGGGCARCCGTCGAACTTG | |
| 1055F | 16S rDNA | Total Bacteria | ATGGCTGTCGTCAGCT | 337 |
| 1392R | | | ACGGGCGGTGTGTAC | |
| 16sTaq1115-BHQ | | | (6-FAM)-CAACGAGCGCAACCC-(TAMARA) | |

Results

Figure 2:
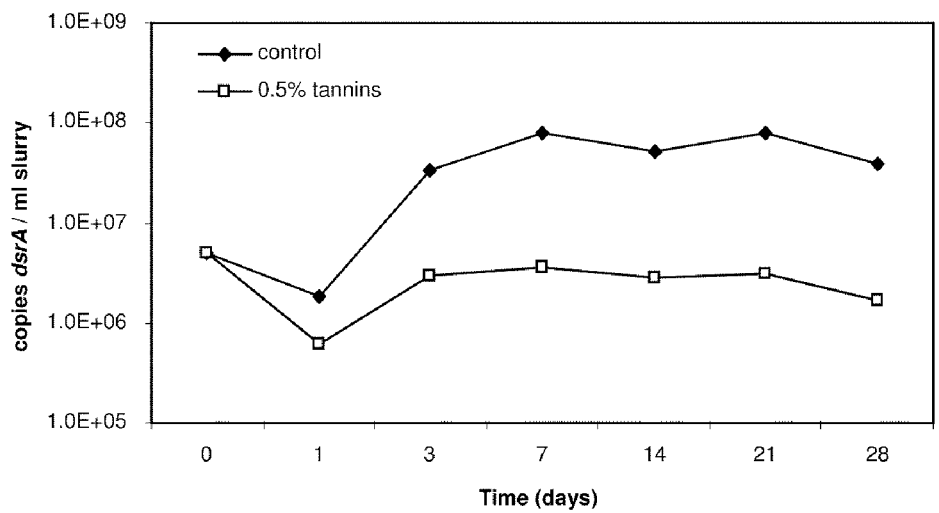
FIG. 2 shows the quantification of total SRB in stored swine manure treated in vitro with 0.5% w/v condensed tannins in Example 1. Data are presented as the sum of the 3 SRB group qRT-PCR assays.

The addition of 0.5% w/v condensed tannins to stored swine manure in vitro significantly reduced the numbers of total SRB by 95% after 7 days of treatment. This reduction was maintained throughout the course of the study (28 days). At the end of the study there were an estimated $1.65 \times 10^6$ cells $ml^{-1}$ total SRB in the tannin treated samples, compared to $3.84 \times 10^7$ cells $ml^{-1}$ total SRB in the control samples, a reduction of 96% (FIG. 2).

The dominant group of SRB in the swine manure was the *Desulfobulbus*-like Group 1, with an estimated $3.71 \times 10^6$ cells $ml^{-1}$ starting population. This group of SRB was reduced by 96% after 7 days of treatment with condensed tannins, and this reduction was maintained over 28 days (FIG. 1).

The *Desulfovibrio*-like Group 3 SRB was also significantly affected by tannin treatment. After just 24 hours of treatment with condensed tannins, the Group 3 SRB were reduced by 80%, from $9.33 \times 10^4$ cells $ml^{-1}$ to $1.9 \times 10^4$ cells $ml^{-1}$ (FIG. 1).

Figure 3:
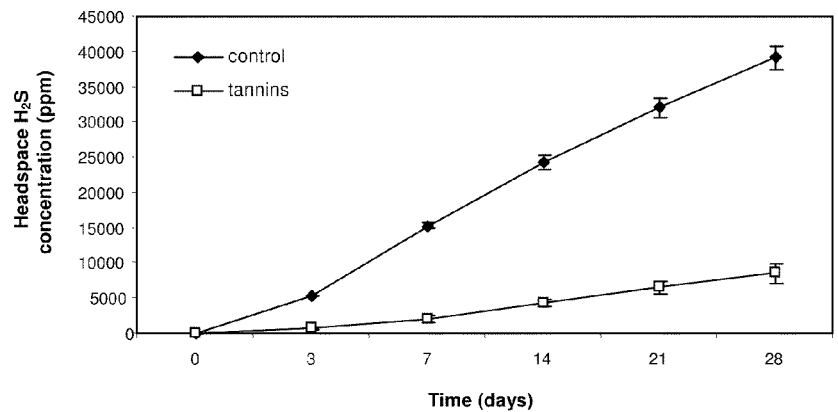
FIG. 3 shows the cumulative $H_2S$ concentration in the headspace gas of serum bottles containing fresh swine manure slurry treated in vitro with 0.5% w/v condensed tannins in Example 1. Each treatment was performed in triplicate and data are presented as the mean of duplicate measurements.
Figure 4:
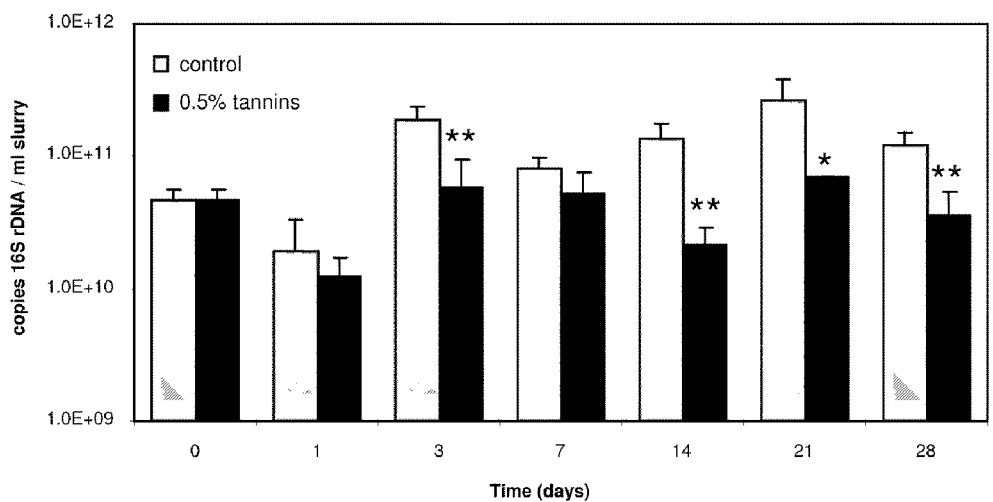
FIG. 4 shows the quantification of total bacteria in stored swine manure treated in vitro with 0.5% w/v condensed tannins in Example 1. Each treatment was performed in triplicate and data are presented as the mean of triplicate qRT-PCR assays. Significance values for comparisons of control versus tannin treatment: *, $P<0.05$; **, $P<0.01$

Hydrogen sulfide production was greatly reduced by treatment with condensed tannins. By the end of the study, $H_2S$ production was reduced by 78% in the tannin treated samples (FIG. 3).

CONCLUSION

This research demonstrates that treatment of stored swine manure in vitro with Quebracho condensed tannins can suppress $H_2S$ production and reduce the population of SRB.

EXAMPLE 2

A variety of tannins from different plants were evaluated for their efficacy in reducing gas production from feces.

Materials and Methods

Swine Manure Samples and In Vitro Incubations

Swine manure slurry and fresh feces were as collected from underground storage pits at a local swine facility in Eureka, Ill. Slurry was diluted in anaerobic buffer to a 10% v/v final solution, and fresh feces was added to 10% w/v final amount. The solution was mixed, and 100 ml aliquots were added to 150 ml serum bottles under a stream of nitrogen. Control bottles were left untreated and immediately sealed. To the remaining samples, 0.1% or 0.5% (measured as weight tannins per volume of feces) of the various condensed tannins (see below) were added, mixed well to dissolve the tannins and then capped and sealed. All bottles were incubated anaerobically at room temperature.

Determination of Gas Production:

Gas production was determined using a Sensym ICT Digital Pressure Gauge (Invensys, Milpitas, Calif.) attached to a 20 gauge hypodermic needle. The pressure was released from each bottle following measurement. Gas production was converted from pressure to milliliters of gas based on head space volume.

Identification of Condensed Tannins:

Quebracho tannin was isolated from the Quebracho plant. C-KPN and C-KPS tannins were isolated from chestnut. NA-1 tannin is a by-product from paper production from spruce trees. Wattle ME tannin was isolated from the bark of the mimosa tree. TARA tannin was isolated from the pods of the Tara tree. All tannins were obtained from Chemtan Co., Inc., Exeter, N.H.

Results

As shown in Table 2, the tannins varied widely in their capacity to reduce gas production from the swine feces. Quebracho tannins significantly reduced gas production in comparison to the other tannins tested, reducing the gas production by more than an order of magnitude than the closest tannin, C-KPN and WE-ME. Interestingly, two of the tannins tested, NA-1 and TARA, actually increased gas production.

TABLE 2

Effects of Addition of Various Condensed Tannins on Total Gas Production by In Vitro Swine Manure Slurries

| Tannin | % Control (Cumulative Gas Production)[1] |
|---|---|
| Control (No Tannin) | 100.0 |
| Quebracho (0.5% w/v) | 2.2 |
| C-KPN (0.1% w/v) | 30.3 |
| C-KPN (0.5% w/v) | 53.2 |
| C-KPS (0.1% w/v) | 39.4 |
| C-KPS (0.5% w/v) | 55.6 |
| NA-1 (0.1% w/v) | 120.2 |
| NA-1 (0.5% w/v) | 188.1 |
| TARA (0.1% w/v) | 130.0 |
| TARA (0.5% w/v) | 155.6 |
| WE-ME (0.1% w/v) | 30.0 |
| WE-ME (0.5% w/v) | 43.0 |

[1]Quebracho tannin experiment terminated after 42 days. Other tannins ended after 58 days.

It is understood that the foregoing detailed description is given merely by way of illustration and that modifications and variations may be made therein without departing from the spirit and scope of the invention.

We claim:

1. A method for treating animal waste comprising applying Quebracho tannins onto animal waste in an amount effective to elicit at least one effect selected from the group consisting of a) reducing total gas emissions therefrom, b) reducing hydrogen sulfide emissions therefrom, c) reducing methane emissions therefrom, d) reducing populations of anaerobic sulfate reducing bacteria therein, and e) reducing the metabolic activity of anaerobic sulfate reducing bacteria therein, wherein said animal waste comprises feces or fecal waste-containing materials.

2. The method of claim 1 wherein said animal waste is contained within a cistern, pit, lagoon, holding pond or settling pond.

3. The method of claim 1 wherein said animal waste further comprises urine.

4. The method of claim 1 wherein said animal waste is substantially solid.

5. The method of claim 1 wherein said animal waste is from swine, bovine, fowl, equine, caprine, ovine, feline, canine, rodentia, leporids, mustelids or zoo animals.

6. The method of claim 1 wherein said animal waste is from swine or bovine.

7. The method of claim 1 wherein said amount of said tannins to said animal waste is between about 0.1% to about 10%, by weight of said tannins per volume of said animal waste.

8. The method of claim 1 wherein said amount of said tannins to said animal waste is between about 0.1% to about 1%, by weight of said tannins per volume of said animal waste.

9. The method of claim 1 wherein said Quebracho tannins comprise Quebracho condensed tannins.

10. The method of claim 1 wherein said anaerobic sulfate reducing bacteria comprise *Desulfovibrio* species and *Desulfobulbus* species.

11. The method of claim 1 wherein said tannins are formulated in a composition with a carrier.

12. The method of claim 11 wherein said composition is a liquid.

13. The method of claim 11 wherein said composition is a solid.

14. The method of claim 1 wherein said applying comprises applying said tannins onto animal litter.

15. A method for reducing odor emissions from animal waste comprising combining Quebracho tannins with animal litter, and applying said litter in the locus of an animal to receive animal waste discharged therefrom, wherein said tannins are provided in an amount effective to elicit at least one effect selected from the group consisting of a) reducing total gas emissions from said animal waste, b) reducing hydrogen sulfide emissions from said animal waste, c) reducing methane emissions from said animal waste, d) reducing populations of anaerobic sulfate reducing bacteria in said animal waste, and e) reducing the metabolic activity of anaerobic sulfate reducing bacteria in said animal waste, and further wherein said animal waste comprises feces.

16. The method of claim 15 wherein said animal is selected from the group consisting of fowl, feline, rodentia, leporids, and mustelids.

17. The method of claim 15 wherein said tannins are mixed with said animal litter.

18. The method of claim 1 wherein said Quebracho tannins are applied onto said animal waste in an amount effective to reduce total gas emissions therefrom.

19. The method of claim 15 wherein said Quebracho tannins are provided in an amount effective to reduce total gas emissions from said animal waste.

* * * * *